US012742760B2

(12) United States Patent
Onghanseng et al.

(10) Patent No.: US 12,742,760 B2
(45) Date of Patent: Sep. 22, 2026

(54) COMPARATIVE METHODS FOR AIR QUALITY MEASUREMENT AND USE THEREOF

(71) Applicant: UHOO PTE LTD, Singapore (SG)

(72) Inventors: Dustin Jefferson S. Onghanseng, Faber Crest (SG); Chun Lai Brian Lin, Hong Kong (CN)

(73) Assignee: UHOO PTE LTD, Singapore (SG)

( * ) Notice: Subject to any disclaimer, the term of this patent is extended or adjusted under 35 U.S.C. 154(b) by 344 days.

(21) Appl. No.: 18/000,196

(22) PCT Filed: Dec. 9, 2020

(86) PCT No.: PCT/SG2020/050731
§ 371 (c)(1),
(2) Date: Nov. 29, 2022

(87) PCT Pub. No.: WO2021/242170
PCT Pub. Date: Dec. 2, 2021

(65) Prior Publication Data

US 2023/0243797 A1 Aug. 3, 2023

(30) Foreign Application Priority Data

May 29, 2020 (SG) ........................... 10202005086U

(51) Int. Cl.
*G01N 33/00* (2006.01)
*F24F 11/32* (2018.01)
(Continued)

(52) U.S. Cl.
CPC .......... *G01N 33/0063* (2013.01); *F24F 11/32* (2018.01); *G01N 33/0031* (2013.01); *G08B 21/12* (2013.01); *F24F 2110/50* (2018.01)

(58) Field of Classification Search
CPC ........... G01N 33/0063; G01N 33/0031; G01N 33/0037; G01N 33/004; G01N 33/0075;
(Continued)

(56) References Cited

U.S. PATENT DOCUMENTS 6,711,470 B1 3/2004 Hartenstein et al.
2008/0182506 A1 7/2008 Jackson et al.
(Continued)

FOREIGN PATENT DOCUMENTS

CN 105628091 A 6/2016
CN 107023947 A 8/2017
(Continued)

OTHER PUBLICATIONS

Coccia, An index to quantify environmental risk of exposure to future epidemics of the COVID-19 and similar viral agents: Theory and practice, Environmental Research 191, pp. 1-7, available online Aug. 29, 2020 (Year: 2020).*
(Continued)

*Primary Examiner* — David Z Huang
(74) *Attorney, Agent, or Firm* — Victor Cardona, Esq; Heslin Rothenberg Farley & Mesiti P.C.

(57) ABSTRACT

A method for categorizing a viral risk within a occupiable space, the method comprising the steps of: measuring environmental data using a plurality of sensors within said occupiable space; determining a virus index for the occupiable space based upon a combination of said environmental data; providing a virus index scale, said scale including environmental categories corresponding to different viral indices; comparing the virus index with the virus index scale, and so; categorizing the viral risk of the occupiable space.

15 Claims, 3 Drawing Sheets

(51) Int. Cl.
*G08B 21/12* (2006.01)
*F24F 110/50* (2018.01)

(58) Field of Classification Search
CPC ..... G01N 33/0062; F24F 11/32; G08B 21/12; G16H 40/20; G16H 50/30
See application file for complete search history.

(56) References Cited

U.S. PATENT DOCUMENTS

| | | | |
|---|---|---|---|
| 2018/0073759 A1* | 3/2018 | Zhang | F24F 11/30 |
| 2019/0035249 A1 | 1/2019 | Mou et al. | |

FOREIGN PATENT DOCUMENTS

| | | |
|---|---|---|
| CN | 107085070 A | 8/2017 |
| CN | 108800427 A | 11/2018 |
| CN | 106225163 B | 4/2019 |
| CN | 109780604 A | 5/2019 |
| WO | 2013065205 A1 | 5/2013 |

OTHER PUBLICATIONS

Environmental Protection Agency, 40 CFR Part 58, Air Quality Index Reporting, Federal Register vol. 64, No. 149, Aug. 4, 1999 (Year: 1999).*

Casanova, L. M. et al., “Effects of air temperature and relative humidity on coronavirus survival on surfaces,” Applied and Environmental Microbiology, 2010, vol. 76(9): pp. 2712-2717.

Hoo Air Sensor Review: Mobile app, IFTTT, URL:https://www.youtube.com/watch?v-eOc-x2yZhe8, 2018.

Schieweck et al., “Smart homes and the control of indoor air quality,” Renewable and Sustainable Energy Reviews, 2018, vol. 94: pp. 705-718.

Ciencewicki et al., “Air pollution and respiratory viral infection,” Inhalation Toxicology, 2007, vol. 19(14): pp. 1135-1146. Abstract only.

Domingo, J. L. et al. Effects of air pollutants on the transmission and severity of respiratory viral infections, Environmental Research, 2020, vol. 187: pp. 109650.

International Search Report and Written Opinion of International Application No. PCT/SG2020/050731, mailed Feb. 19, 2021, 11 pages.

Intellectual Property Office of Singapore, Search Report, Jul. 22, 2025, 2 pages.

* cited by examiner

COMPARATIVE METHODS FOR AIR QUALITY MEASUREMENT AND USE THEREOF

CROSS REFERENCE TO RELATED APPLICATIONS

This application is a national stage filing under Section 371 of International Application No. PCT/SG2020/050731, filed Dec. 9, 2020, published in English on Dec. 2, 2021, as WO 2021/242170 and which claims priority from Singapore patent application Ser. No. 10/202,005086U filed on May 29, 2020, the entire disclosures of which are incorporated herein by reference.

FIELD OF THE INVENTION

The invention relates to the measurement of air quality parameters in an occupiable space. In particular, the invention relates to use of such parameters to improve air quality in said occupiable space.

BACKGROUND

Residential, commercial and educational facilities represent excellent opportunities for the spread of disease, given the enclosed spaces, and close human interaction. Whilst these facilities may include HVAC systems, such systems do not, in themselves, mitigate the spread of virus and bacteria. In fact, without a measure as to the risk posed, HVAC may even facilitate viral and bacterial spread through providing ideal conditions for a high survival and spread rate.

SUMMARY OF INVENTION

In a first aspect, the invention provides a method for categorizing a viral risk within a occupiable space, the method comprising the steps of: measuring environmental data using a plurality of sensors within said occupiable space; determining a virus index for the occupiable space based upon a combination of said environmental data; providing a virus index scale, said scale including environmental categories corresponding to different viral indices; comparing the virus index with the virus index scale, and so; categorizing the viral risk of the occupiable space.

In a second aspect, the invention provides a system for categorizing a viral risk within a occupiable space, the system comprising: a plurality of sensors arranged to measure environmental data within said occupiable space; a determination unit arranged to determine a virus index for the occupiable space based upon a combination of said environmental data; a virus index scale, said scale including environmental categories corresponding to different viral indices; a comparison unit arranged to compare the virus index with the virus index scale, and further arranged to categorize the viral risk of the occupiable space.

A viral risk for instance may be defined by several key factors, in a) The environmental conditions that may promote the time of survival, and;
b) The ease by which the virus may be transported by air, both in terms of the environmental conditions mentioned in (a) as well as the flow rate within the space.
c) The ease by which the virus may be transmitted via touch if the virus stays/survives on a surface (i.e. table, chair, laptop, etc.).

For instance, having an environment where the viral risk is low in a first space, but the rate at which the virus may be transported by air, as well as the survival rate, may lead to a subsequent space becoming contaminated.

The invention therefore provides a means of determining an index that may provide an objective measure for viral risk based upon measuring a series of environmental parameters to collect environmental data aimed at one or both of the factors mentioned above.

Further, the invention may further include a pre-determined virus index scale, perhaps ranging from 1 to 10, with each increment, or a range of increments, of the index indicating a different virus risk state for the space under consideration. This information may then be provided to key stakeholders for information purposes or for corrective action should the scale indicate a threshold has been exceeded.

BRIEF DESCRIPTION OF DRAWINGS

It will be convenient to further describe the present invention with respect to the accompanying drawings that illustrate possible arrangements of the invention. Other arrangements of the invention are possible and consequently, the particularity of the accompanying drawings is not to be understood as superseding the generality of the preceding description of the invention.

DETAILED DESCRIPTION

The invention is directed to the identification of a viral risk within an occupiable space. Such an occupiable space may be:

i) Indoor including confined spaces for residential, commercial and industrial use;
ii) Outdoor including open areas, amphitheatres, alfresco dining areas
iii) Quasi-indoor/outdoor area such as courtyards and open-air restaurants, and;
iv) Transitory spaces having short term occupation, and perhaps include environments conducive to a high virus index, such as cool rooms, control rooms and lift shafts.

In terms of viral risk, this may include conditions where virus has favorable conditions to grow on a surface. Viral risk may further apply to the risk of airborne virus being widely distributed through the occupiable space. This may be a function of distribution by airflow, providing speed of transport, and conditions which promote the virus remaining active for an extended period, such that the distribution of the active virus can reach substantial proportion of the occupiable space.

The invention relates to two systems which may be used in isolation or together.

Figure 1:
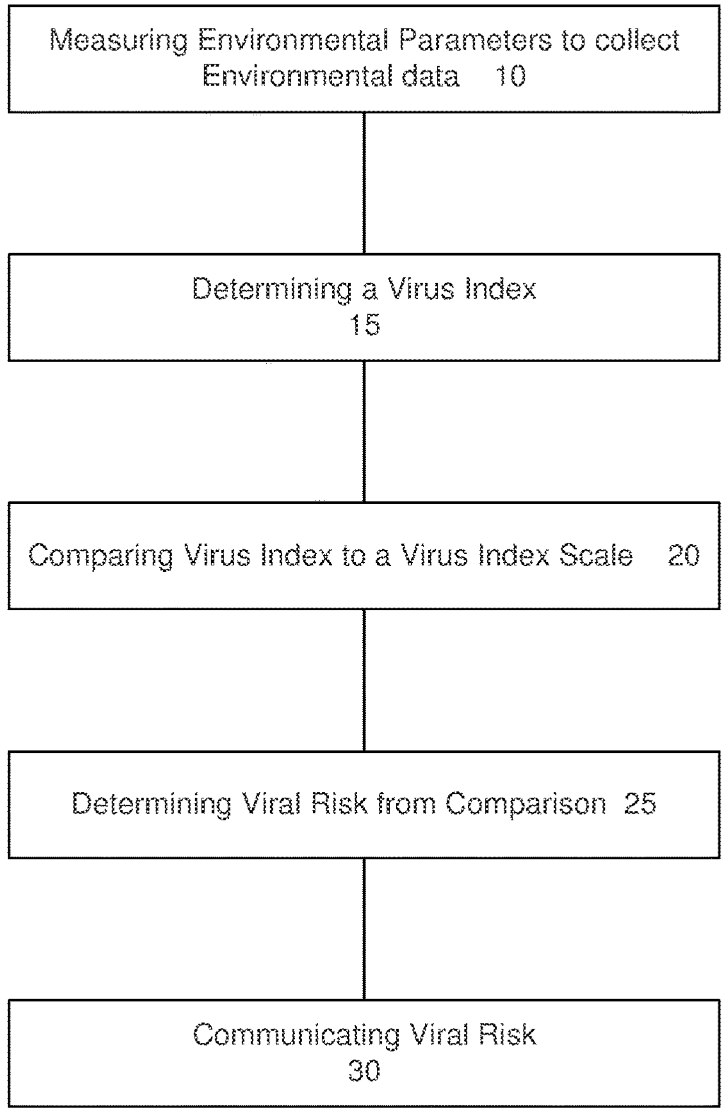
FIG. 1 is a flow chart for a process according to one embodiment of the present invention.

Firstly, and as shown in FIG. 1, data is measured 10 from a plurality of sensors located about an occupiable space. The sensors may be interconnected to form a sensor array, or may be existing sensors which are subsequently connected to form a system upon which data is collected. The occupiable space may have a residential, commercial, industrial or educational function. A virus index for that occupiable space is determined 15 by a determination unit based upon the measured environmental data, and is subsequently compared to a Virus Index Scale, providing a rating or category for each Virus Index, or a range of indices. Then, the index and/or the comparison with the pre-determined scale, is then communicated to the various stakeholders. The comparison may then define a viral risk for the occupiable space. When communicated, the various stakeholders may then decide upon a suitable cause of action.

Secondly, on receiving a virus index and a comparison made with the pre-determined scale, the communication step may include sending a signal to a control system in operational communication with various plant and equipment. The control system may then assess the operational steps required to reduce a risk, from mild to severe, including any other condition other than safe/good. The system may be further triggered to pre-empt a viral risk such that, even though the rating is good, it may be desired to further reduce the risk and prevent it from going to mild risk. i.e. index of 1 to 3 is good, but when it's at 3, people may already trigger action to bring it down to 1 or 2.

The control system may act autonomously to operate the plant and equipment to control the virus index. Alternatively, the control system may be used by an operator to exercise control over the plant and equipment. Alternatively, the control system may provide the assessed operational steps to the operator, for approval or for manual operation.

It will be appreciated that any one, or a combination, of the determination unit, comparison unit and communication unit may form part of the control system.

Figure 2:
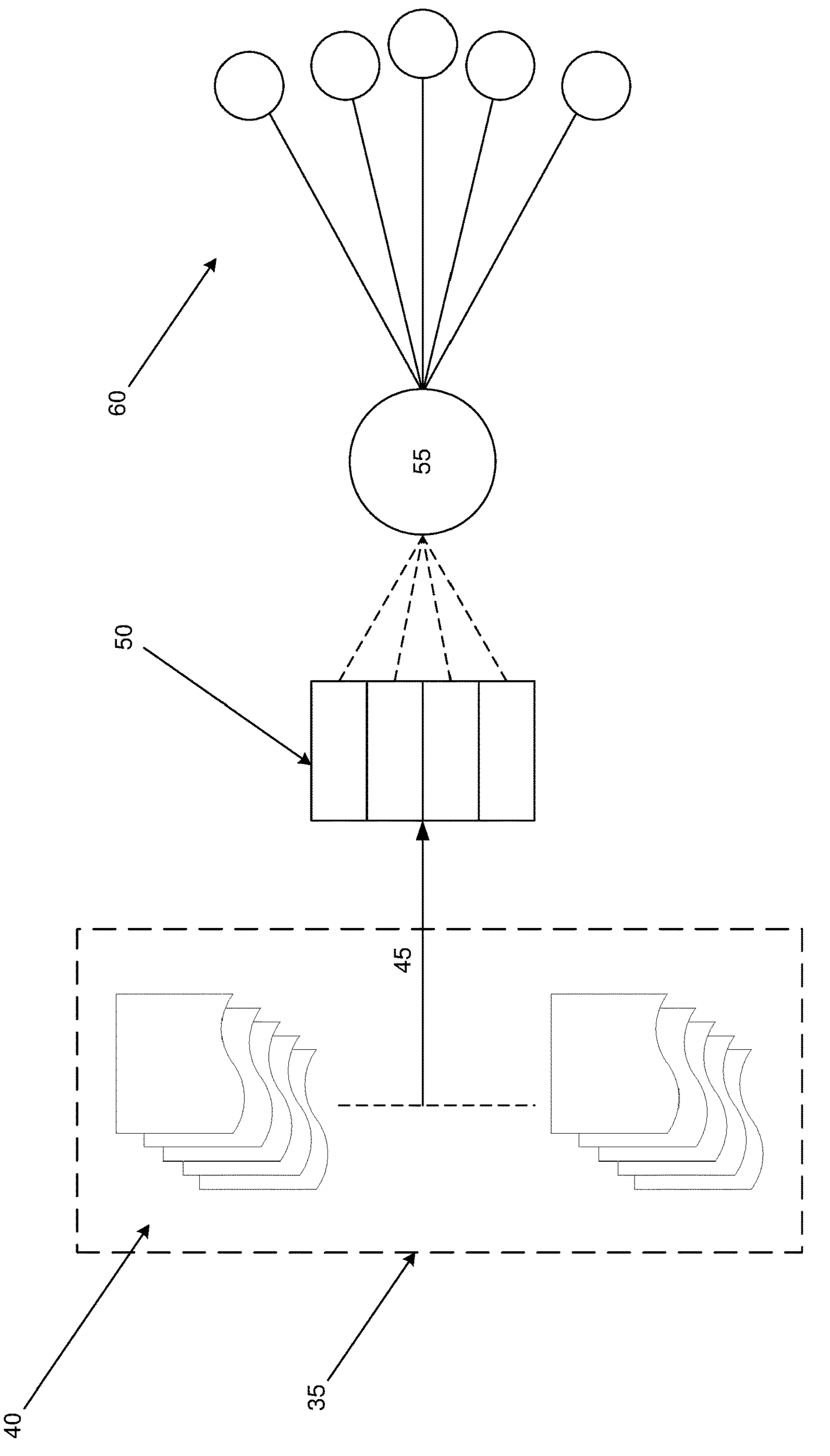
FIG. 2 is a schematic view of virus index comparison system according to one embodiment of the present invention.

Referring to FIG. 2, an occupiable space 35, according to one embodiment, may be a large atrium type arrangement such as an amphitheatre, lecture hall or library. It may also extend to an indoor space having a plurality of sub-zones, such an office building with multiple offices. In either case, the virus may be distributed through an HVAC system, or stay suspended in the air in one location, or simply move from one area to another or from one space to another by floating in the air (without going through the HVAC). Using a sensor array 40, it will be appreciated that the environmental data collected in one or more locations within the occupiable space, or within each sub-zone, or within the HVAC system. The data from each location may be used separately, or in combination, in order to determine measured environmental parameters in said occupiable space, sub-zones of the occupiable space, or HVAC system active within said occupiable space.

In one embodiment, having measured the environmental parameters, the data may be used to generate a virus index, or simply a virus index, being a dimensionless measure of the ability of the virus to survive within the occupiable space. The index based upon the measured data is then compared 45, a comparison unit, to a virus index scale 50 providing a measure of the ability of the virus to propagate. An example of said virus index scale is shown in Table 1 below.

In a further embodiment, the comparison unit may then communicate 60 the measured viral index to a communication module 55. For instance, the index and/or comparison may be publicly displayed for use within the occupiable space. For instance, a device or screen may include;

i) A colour based on the risk, for instance:
   a. green where the viral risk is in a range that is considered safe or good,
   b. yellow and/or orange for risks between safe and unsafe, or for a rapidly changing risk, and
   c. red for a severe or unsafe risk;

ii) A number corresponding to the virus index;

iii) An aural warning such as an alarm, or recorded audio message, when the viral risk is unsafe, or rapidly changing;

iv) A visual warning including on a digital screen (e.g. phone, laptop, television, public display screen etc), providing text corresponding to a descriptor from the virus index scale corresponding to the current viral risk, or;

v) A combination of any of the above.

Alternatively, a system according to the present invention may digitally communicate the index and/or comparison, such as through the internet, SMS or various forms of social media. Interested parties for receiving said index and/or comparison may also include management personnel responsible for managing the occupiable space. Said management personnel may also include those authorized to control various plant and equipment. Said plant and equipment may include air handling units, external ventilation, louvres, HVAC systems or other such plant and equipment which may affect any/or all of the environmental perimeters used to determine the index.

Figure 3:
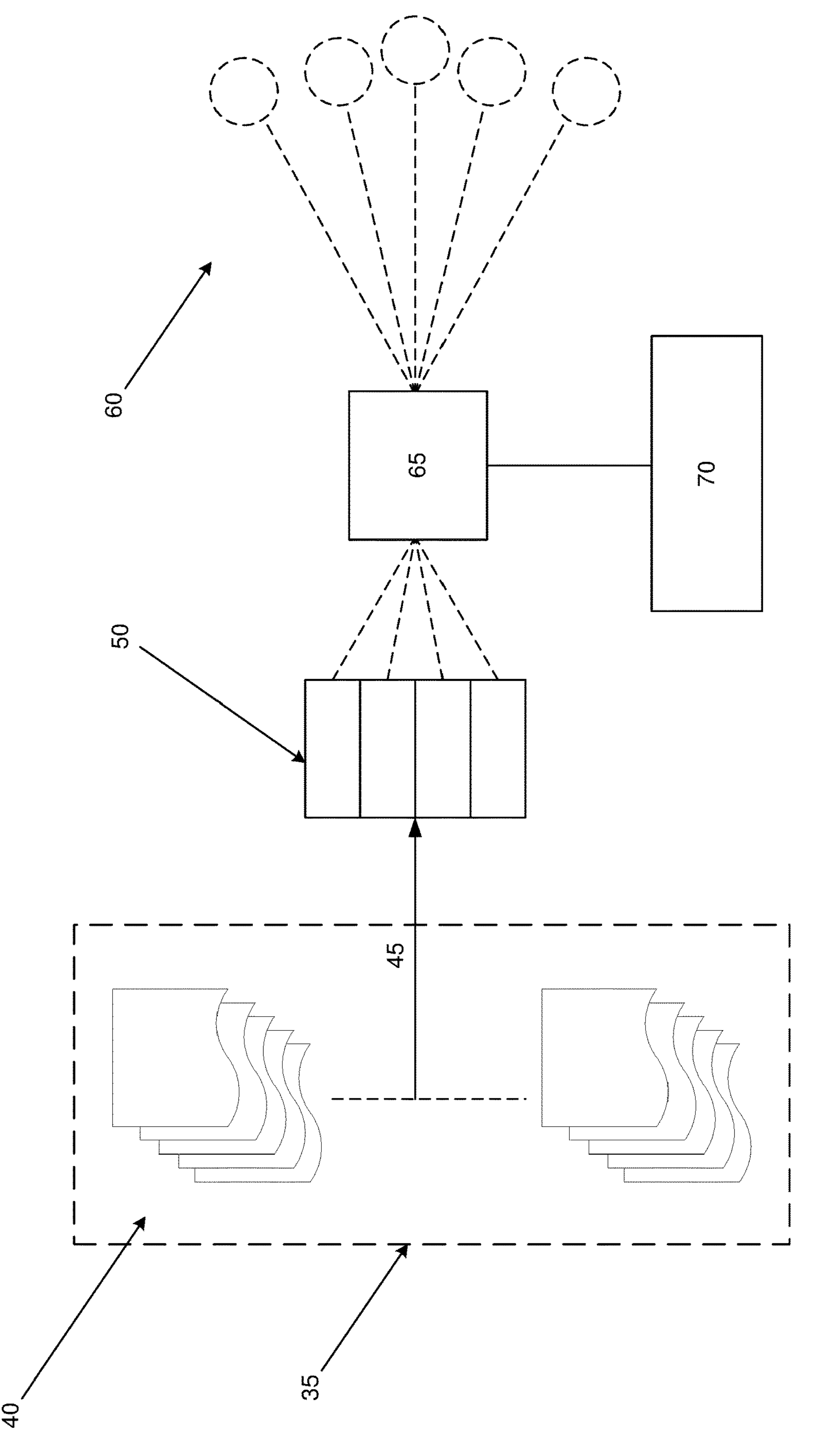
FIG. 3 is a schematic view of virus index comparison system according to a further embodiment of the present invention.

Shown in FIG. 3 is a further embodiment, where the sensor array 40 collects data within the occupiable space and makes the comparison as discussed above. Instead of a communication unit, the virus index and comparison are sent to a control system 65 to be used to operate plant and equipment in a manner to control the virus index. The index and/or comparison may be used by the control system 65 which may automatically control said plant and equipment 70, either autonomously or semi-autonomously, such as requiring final approval to make changes to the plant and equipment.

In one embodiment, the sensor array may measure any one or a combination of parameters including temperature and humidity. Further embodiments may also include measuring other parameters, including any one or a combination of $CO_2$, carbon monoxide, Particulate Matter (of various sizes), nitrogen dioxide, ozone, air pressure, within the occupiable space and VOCs. It will be appreciated that, for the purposes of determining the virus index, the important parameters may include temperature and humidity. Other parameters may add further accuracy, situational relevance, viral applicability and/or location specific necessity to the determined virus index, such as PM2.5, PM1, nitrogen dioxide, and $CO_2$.

When the parameters are taken in isolation, ideal ranges are provided below. The Virus Index is directed to assessing the combination of these parameters so as to affect decision making and implement appropriate action.

1 Temperature: 19° C. to 24° C.

The infection rate of viruses is significantly reduced at room temperature (20° C.) compared to colder temperatures (e.g. 4° C.). Whereas, at warmer temperatures (30° C.), transmission of influenza viruses is blocked or becomes highly inefficient. Maintaining temperature at the ideal level not only lessens the risk of virus transmission but also keeps people comfortable indoors.

2. Relative Humidity: 40%-60%

In environments with lower than 40% Relative Humidity (RH), droplets from a cough or a sneeze lose their moisture quickly. This results in droplets becoming 'dry aerosols' and capable of staying in the air for longer periods. Viral particles remain infectious much longer below 40% and above 80%. Virus particles are most inactive at 50% humidity, and retain their infectiousness the further from that median value, plateauing at 20% and 80%, respectively. Staying within 40% to 60% relative humidity is ideal from a comfort perspective but 50% is the most ideal in terms of fast virus inactivation. Keeping the humidity at the ideal range not only helps people stay comfortable but also keeps people healthy. Low humidity (less than 30%) may promote dry nasal passage which makes people more susceptible to cold viruses while high humidity (more than 70%) may promote mold growth which can be harmful to people with weakened immune systems.

3. PM2.5: Below 15 μg/m3

Particulate Matter also known as "Particle Pollution" is a complex mixture of extremely small particles and liquid droplets. Particulate Matter at 2.5 microns in size or smaller can be inhaled deep into the lungs and cause irritation and corrosion of the alveolar wall, which impairs lung function. These particles are small enough to stay suspended in the air. An increased vulnerability to influenza-like illnesses when levels of PM2.5 were above the ideal range. Data suggest that PM2.5 stays airborne longer, creating a "condensation nuclei" which virus droplets attach to. These are then inhaled by people, resulting in infection. Thus, it is best to keep PM2.5 levels low to minimize risk of infection. Examples of sources of PM2.5 indoors: smoking, cooking, candles, space heaters, furnaces, and poorly-maintained HVAC system.

4. Carbon Dioxide: Below 800 ppm

Carbon Dioxide has long been used as an indicator of good indoor air quality primarily because of its association with ventilation. When carbon dioxide levels are high, it may indicate that the space is not well ventilated. The ideal level of $CO_2$ is needed to reduce the risk of lung inflammation. Chronic inflammation caused by persistent high $CO_2$ levels is not ideal for health. Moreover, longer exposure to high $CO_2$ can cause fatigue, headaches, and dizziness. It is also possible to develop hypercapnia acidosis, characterized by increased levels of carbon dioxide in the blood. This may suppress immune function and may make one more susceptible to disease. Some causes of carbon dioxide elevation indoors: improperly maintained combustion devices and poor ventilation.

5. Nitrogen Dioxide ($NO_2$): Below 53 ppb

High levels of Nitrogen Dioxide indoors may result from outdoor $NO_2$ entering an indoor environment as well as combustion sources inside the home/workplace. Short-term exposure may irritate airways while long-term exposure may lead to chronic illness and respiratory infections with viruses. Asthmatics may also experience longer symptomatic periods and increased medication use for children. Examples of sources of nitrogen dioxide: Automobiles from attached garage or near a busy street, appliances with defective installations, gas stoves, kerosene heaters, chimneys, etc.

The sensor array may reside within a single device strategically placed to provide an optimize collection of data.

Alternatively, one or more sensors within the sensor array may be remote from the other sensors. Such isolated sensors may direct data to the Determination Unit in a wired or wireless fashion, including via the internet.

Data is processed when the sensor senses the air and outputs raw data from it. The raw data may be retrieved via firmware of the Determination Unit, and calibrated using algorithms based on scientific analysis of sensor responses and characteristic in specific laboratory settings. Accuracy of calibrated data may be enhanced by giving a tighter tolerance. For example, if the original temperature sensor has a tolerance/accuracy of plus minus 0.5° C.

Firmware calibrated data may be further processed in a cloud-based server. Calibrated Data may be stored in a database and tagged to every device to which the system for which the sensor reading is associated with the serial number of the device so it can be retrieved from the database. Calibrated Data may be accessible by the user when they login to their accounts in a respective app or dashboard.

In determining the Virus Index, several data processing techniques may be used. The algorithm used to generate the Virus Index may vary on the data being used, and the application of the eventual index. For instance, such processing may include:

i) Time period based rolling averages, for various time periods, for example, 1 s, 5 s, 1 min, 5 min, 60 mins etc;

ii) Weighted time-based rolling average, where a factor is applied to the most recent data. This may be useful where conditions are changing rapidly, with the most recent data being more relevant;

iii) Parameter weighted, whereby each parameter is weighted according to its relative importance for the index being determined. This alternative may then use either (i) or (ii) in addition to the respective weighted parameter;

iv) An empirical formula based upon a combination of a regression of each of at least two environmental parameters, or;

v) Some other formulation relevant to the parameter being used and the application of the index.

The system, in determining the index, may communicate advisory communications (email, sms, whatsapp, etc.) to users, such as, "$CO_2$ levels are too high, adjust your ventilation system to bring in fresh air." or "Humidity is above 70% for 5 hours now, mold may start to form in your living room. Switch on a dehumidifier."

The system may be directed to providing thresholds which are tighter/stricter compared to standard air quality safety thresholds. Standard air quality safety thresholds may be based on triggering health ailments when exposed to a certain period of time. As an example, the thresholds for the Virus Index may be directed to the survival rate of virus in the air. It may be made stricter/tighter to make viruses inactive. The Virus Index combines these parameters into one number that indicates the likelihood of virus propagation/activation/survival, which need to be assessed based on multiple parameters all at once and not one parameter at a time. The Virus Index is not a summation, but a combination.

For example, when humidity levels are at 80%, the system triggers a dehumidifier to switch on and bring humidity down. Once the ideal humidity level based on the Virus Index is reached, which may be 50%, the system can automatically trigger to switch off the dehumidifier.

An example of a Virus Index Scale may be found in Table 1. In this case, the highest score is 10. The lower the score, the better.

TABLE 1

| Virus Index Scale | | | |
|---|---|---|---|
| Good (1-3) | Mild (4-6) | Bad (7-8) | Severe (9-10) |
| Virus survival is low and spreading of the virus in the air unlikely. | Virus survival is moderate and the virus spreading in the air is possible but air quality poses little to almost no direct health risk for people who are usually not sensitive to air pollution. Sensitive people may experience health effects. More attention to air quality should be given and actions to improve air quality is recommended. | Virus survival is prolonged and likelihood of the virus spreading in the air is higher. Air quality poses some health risk. Critical assessment of your air quality is necessary and actions to improve air quality is required. | Virus survival is high and the virus spreading in the air is likely. Air quality would affect most people and actions to improve air quality is necessary. |

Isometric lines alone will not indicate the overall picture because it means the information, when viewed in isolation from other parameters is incomplete and misleading.

This silo view is removed and analysis is performed on all parameters together to provide one index.

For the various parameters described, the plant and equipment operated by the Determination Unit, based upon the index include, but not limited to:

Temperature: Air handling unit

Humidity: A dehumidifier

PM1 and PM2.5: Each of an air purifier, air filter, ventilation $CO_2$: Ventilation equipment including range hood in the kitchen, exhaust in toilets, windows across the house, HVAC across the house/building, air intake louvers etc.

$NO_2$: Specially modified air purifiers with carbon filter, as well as ventilation equipment as described above, closing windows, removing combustion or burning things in the home/office/building

The invention claimed is:

1. A method for categorizing a viral risk within a occupiable space, the method comprising the steps of:

measuring environmental data using a plurality of sensors within said occupiable space;

determining a virus index for the occupiable space based upon a combination of said environmental data;

providing a virus index scale, said scale including environmental categories corresponding to different viral indices;

comparing the virus index with the virus index scale, and so;

categorizing the viral risk of the occupiable space as a single number; and communicating the viral risk to stakeholders, wherein the communicating step includes a step of sending a signal to a control system, said control system then assessing operational steps required to maintain a safe viral risk condition of the space based on the viral risk, and wherein the safe viral risk condition occurs when temperature is in the range of 19° C. to 24° C., and relative humidity is in the range of 40% to 60%.

2. The method according to claim 1, wherein the communicating step includes displaying any one or a combination of colour, virus index, visual display or aural warning, corresponding to the viral risk.

3. The method according to claim 1, wherein the communicating step includes said control system then assessing operational steps required to reduce the viral risk.

4. The method according to claim 3, further including the step of the control system operating equipment to reduce the viral risk of the space when the viral risk is categorized as not safe.

5. The method according to claim 1, further including the step of the control system operating equipment to reduce a viral risk of the space when the viral risk is categorized as not safe.

6. The method according to claim 1, wherein the environmental data includes levels for at least temperature and humidity.

7. The method according to claim 6, wherein the environmental data further includes levels for any one or a combination of: PM2.5, PM1, nitrogen dioxide, and $CO_2$.

8. The method according to claim 1, wherein the virus index correlates to assessment of virus survival and virus transmission.

9. A system for categorizing a viral risk within a occupiable space, the system comprising:

a plurality of sensors arranged to measure environmental data within said occupiable space;

a determination unit arranged to determine a virus index for the occupiable space based upon a combination of said environmental data;

a virus index scale, said scale including environmental categories corresponding to different viral indices;

a comparison unit arranged to compare the virus index with the virus index scale, and further arranged to categorize the viral risk of the occupiable space as a single number; and communicating, the viral risk to a control system to maintain a safe viral risk condition, wherein the safe viral risk condition occurs when temperature is in the range of 19° C. to 24° C. and relative humidity is in the range of 40% to 60%.

10. The system according to claim 9, further including a communication unit arranged to communicate the viral risk to stakeholders.

11. The system according to claim 10, wherein the communication unit includes a public display system arranged to display any one or a combination of colour, virus index or sound, corresponding to the viral risk.

12. The system according to claim 10, wherein the communication unit is arranged to send a signal to a control system; said control system arranged to assess operational steps required to reduce a viral risk of the space when the viral risk is categorized as not safe.

13. The system according to claim 12, wherein the control system is arranged to operate equipment to reduce virus survival within the space.

14. The system according to claim 9, wherein the environmental data includes levels for at least temperature and humidity.

15. The system according to claim 14, wherein the environmental data further includes levels for any one or a combination of: PM2.5, PM1, nitrogen dioxide, and $CO_2$.

* * * * *